(12) United States Patent
Widlund et al.

(10) Patent No.: US 7,572,250 B2
(45) Date of Patent: Aug. 11, 2009

(54) ABSORBENT ARTICLE

(75) Inventors: Urban Widlund, Pixbo (SE); Eva Simmons, Mölndal (SE); Anders Gustafsson, Billdal (SE)

(73) Assignee: SCA Hygiene Products AB, Gothenburg (SE)

( * ) Notice: Subject to any disclaimer, the term of this patent is extended or adjusted under 35 U.S.C. 154(b) by 435 days.

(21) Appl. No.: 10/292,626

(22) Filed: Nov. 13, 2002

(65) Prior Publication Data
US 2003/0105447 A1    Jun. 5, 2003

Related U.S. Application Data

(60) Provisional application No. 60/337,166, filed on Dec. 10, 2001.

(30) Foreign Application Priority Data
Nov. 30, 2001    (SE) .................. 0104029

(51) Int. Cl.
*A61F 13/20* (2006.01)
(52) U.S. Cl. ............. 604/385.25; 604/362; 604/385.28; 604/385.14; 604/385.26; 604/385.29; 604/385.3; 604/386; 604/367; 604/399; 604/394; 604/391; 604/389; 604/387; 604/390; 604/385.22
(58) Field of Classification Search ............ 604/385.25, 604/385.28, 385.14, 385.26, 362, 386, 367, 604/385.3, 385.29, 399, 394, 391, 389, 387, 604/390, 385.22
See application file for complete search history.

(56) References Cited

U.S. PATENT DOCUMENTS 2,893,393 A    7/1959 Pressley 3,886,941 A    6/1975 Duane et al.

(Continued)

FOREIGN PATENT DOCUMENTS

EP    0 263 720 A1    4/1988

(Continued)

OTHER PUBLICATIONS

International Preliminary Examination Report from PCT/SE02/02204.

*Primary Examiner*—Tatyana Zalukaeva
*Assistant Examiner*—Ginger T Chapman
(74) *Attorney, Agent, or Firm*—Buchanan Ingersoll & Rooney PC

(57) ABSTRACT

An absorbent product has a fluid permeable top sheet, a fluid impermeable backing sheet, and an absorbent core having an upper side, a bottom side, two longitudinally running sides and two laterally running sides. The product further has two longitudinally running barrier flaps at the longitudinally running sides of the absorbent core. The top sheet covers the upper side of the absorbent core. The top sheet, with the upper side of the absorbent core, also covers the longitudinally running sides of the absorbent core and part of the bottom side of the absorbent core, the top sheet extending between at least a portion of the bottom side of the absorbent core and the backing sheet. The top sheet is connected to the backing sheet at the bottom side of the absorbent core. The barrier flaps are connected to the backing sheet at the longitudinally running sides of the absorbent core.

14 Claims, 3 Drawing Sheets

U.S. PATENT DOCUMENTS

Figure 1:
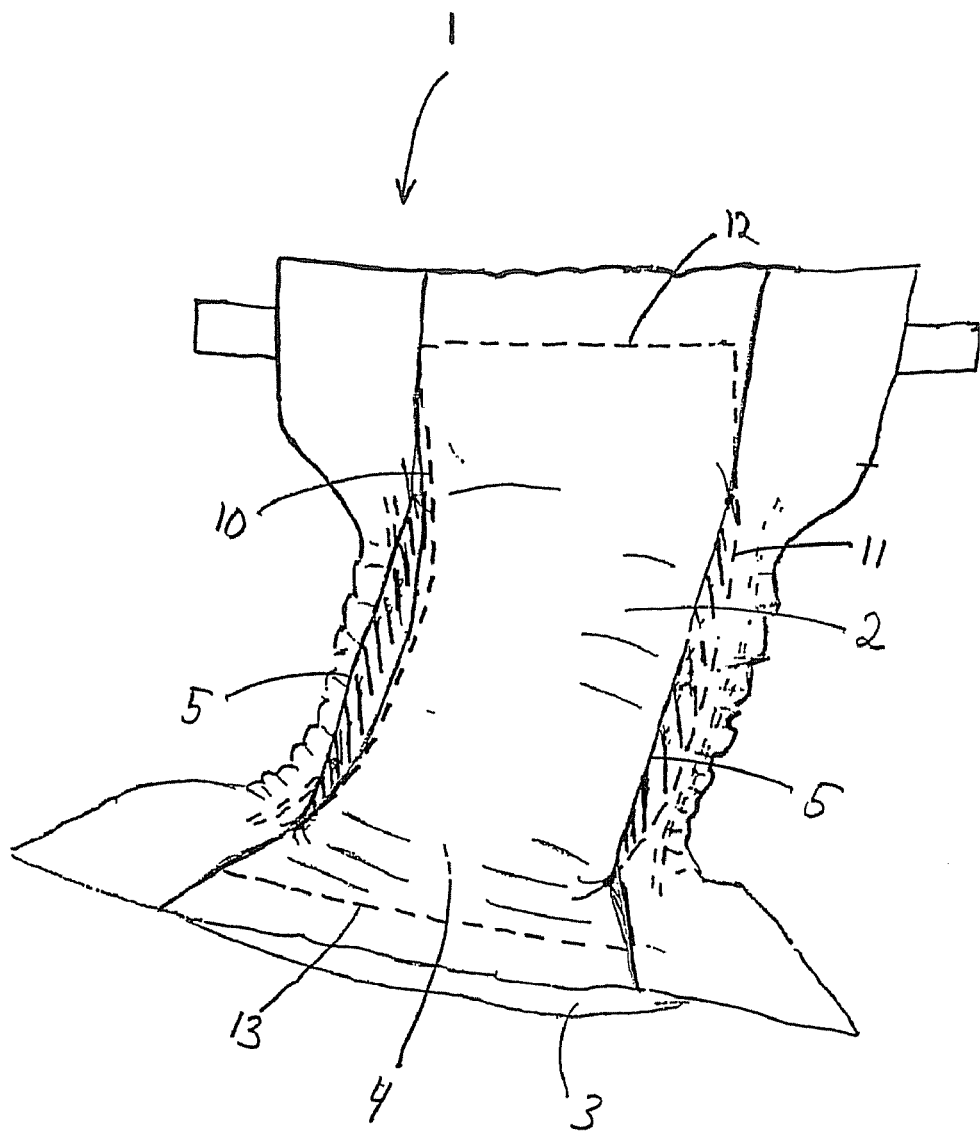

| | | | |
|---|---|---|---|
| 3,926,189 A | | 12/1975 | Taylor |
| 4,090,515 A | * | 5/1978 | Karami ....................... 604/370 |
| 4,578,073 A | * | 3/1986 | Dysart et al. ................. 604/397 |
| 4,623,342 A | * | 11/1986 | Ito et al. ................. 604/385.23 |
| 4,704,115 A | * | 11/1987 | Buell .................... 604/385.26 |
| 4,892,598 A | | 1/1990 | Stevens et al. |
| 5,019,068 A | | 5/1991 | Perez et al. |
| 5,217,447 A | * | 6/1993 | Gagnon ....................... 604/397 |
| 5,234,422 A | * | 8/1993 | Sneller et al. .......... 604/385.25 |
| 5,269,775 A | * | 12/1993 | Freeland et al. ........ 604/385.22 |
| 5,360,422 A | * | 11/1994 | Brownlee et al. ...... 604/385.15 |
| 5,403,303 A | * | 4/1995 | Beplate ....................... 604/394 |
| 5,407,438 A | | 4/1995 | Hedlund et al. |
| 5,458,591 A | | 10/1995 | Roessler et al. |
| 5,476,457 A | | 12/1995 | Roessler et al. |
| 5,476,458 A | * | 12/1995 | Glaug et al. ................. 604/378 |
| 5,599,417 A | | 2/1997 | Glaug et al. |
| 5,601,544 A | | 2/1997 | Glaug et al. |
| 5,891,120 A | * | 4/1999 | Chmielewski ............. 604/378 |
| 6,102,892 A | * | 8/2000 | Putzer et al. ........... 604/385.01 |
| 6,102,900 A | * | 8/2000 | Roessler et al. ........ 604/385.24 |
| 2002/0169432 A1 | * | 11/2002 | Fell et al. ................ 604/385.14 |

FOREIGN PATENT DOCUMENTS

| | | | |
|---|---|---|---|
| EP | 0 945 110 A2 | * | 9/1999 |
| EP | 0 951 890 A2 | * | 10/1999 |
| GB | 2 188 532 A | | 10/1987 |
| GB | 2 256 803 A | | 12/1992 |
| WO | 93/10733 | | 6/1993 |
| WO | 94/03137 | | 2/1994 |
| WO | 94/18927 | | 9/1994 |
| WO | 96/26698 | | 9/1996 |
| WO | WO 02/080834 | * | 10/2002 |

* cited by examiner

ABSORBENT ARTICLE

CROSS-REFERENCE TO RELATED APPLICATIONS

The present application claims the benefit under 35 U.S.C. §119 of U.S. Provisional Application No. 60/337,166, filed in the United States on Dec. 10, 2001, and to Swedish Application No. 0104029-4, filed in Sweden on Nov. 30, 2001, the entire contents of which are hereby incorporated herein by reference.

BACKGROUND OF THE APPLICATION

1. Technical Field

The invention concerns an absorbent product, such as a diaper, an incontinence protection or the like, comprising a fluid permeable top sheet, a fluid impermeable backing sheet facing away from the wearer at use, an absorbent core, positioned between the wearer and the backing sheet, which absorbent core has an upper side, facing the wearer at use, a bottom side, facing away from the wearer at use, two longitudinally running sides and two laterally running sides, whereby the product further comprises two longitudinally running barrier flaps at the longitudinally running sides of the absorbent core, and whereby the top sheet covers the upper side of the absorbent core.

2. Technical Background

The diapers that are available today on the market have been developed to fulfil a number of demands and expectations of the consumers. For instance, it is important that they have a good fit, a good absorption capacity, and that they have reliable and high-qualitative fastening systems.

Conventional diapers are often manufactured in such a way that they have a fluid permeable top sheet facing the user, and a fluid impermeable backing sheet facing away from the user. Between these sheets an absorbent core is placed. The top sheet and the backing sheet are normally applied to each other in the area outside the absorbent core and to the leg elastics of diaper along the longitudinal sides of the absorbent core. In this way, liquid that has been given off may penetrate the top sheet and get into the absorbent core, without the risk of coming out of the absorbent product. The good absorption capacity is achieved by using highly absorbent material in the absorbent core of the diaper, for example superabsorbents, which have a very large capacity to absorb fluid.

However, it will take some time from the moment fluid is given off of the wearer until it reaches the highly absorbent material in the core and is stored there, since the transport of fluid into the material, as well as the absorption of fluid by the superabsorbents, take time. Accordingly, it is important that all fluid that is given off also reaches the highly absorbent material, for leakage not to occur. For this reason leg elastics have been developed, so that the diaper closes around the legs of the wearer, and makes it difficult for fluid to come out of the absorbent product.

In U.S. Pat. No. 5,403,303 a diaper is disclosed which has a pocket-like space between the absorbent core and an outer barrier sheet. The purpose of this space is to function as a reservoir when the absorbent core has not absorbed all fluid, i.e. during the time the fluid is transported into and is stored within the absorbent core.

So called barrier flaps (or standing gathers) have been developed, which run in parallel to the leg elastics. The purpose of the flaps is to function as a barrier for the fluid and to prevent it from leaking out of the diaper.

However, it has been shown that these barrier flaps not always are sufficient. If for example the wearer lies down on the side, fluid that recently has been given off may bear on e.g. one of the barrier flaps and may in certain cases flow over the flap and out of the diaper. Accordingly, it would be desirable to provide a product solving this leakage problem in an effective manner.

SUMMARY

The inventors have now solved this problem by the provision of an absorbent product, such as a diaper, an incontinence protection or the like, comprising a fluid permeable top sheet, a fluid impermeable backing sheet facing away from the wearer at use, an absorbent core, positioned between the wearer and the backing sheet, which absorbent core has an upper side, facing the wearer at use, a bottom side, facing away from the wearer at use, two longitudinally running sides and two laterally running sides, whereby the product further comprises two longitudinally running barrier flaps at the longitudinally running sides of the absorbent core, and whereby the top sheet covers the upper side of the absorbent core, wherein the top sheet, in addition to the upper side of the absorbent core, also covers at least the longitudinally running sides of the absorbent core and a part of the bottom side of the absorbent core, the top sheet has at least one connection to the backing sheet at the bottom side of the absorbent core, the top sheet extending between at least a portion of the bottom side of the absorbent core and the backing sheet and, and the barrier flaps are connected to the backing sheet at the longitudinally running sides of the absorbent core.

Hereby, fluid may be absorbed also from the sides of, and in one embodiment also from beneath, the absorbent core, whereby the potential flow area of the fluid to the absorbent core is increased. Moreover, the volume in the absorbent product that has the capacity to hold fluid before penetrating the absorbent core is increased. Furthermore, the fluid will lie lower in the absorbent product, which reduces the risk for leakage. As a result a better control of the given-off fluid is acquired. In this way, the fluid is immobilised by being prevented to come out of the absorbent product during spreading and storage.

It is also important that the absorbent core is kept in position, which is achieved by that the top sheet and the backing sheet are attached to each other with at least one connection.

SHORT DESCRIPTION OF THE DRAWINGS

In FIG. 1 a conventional diaper with barrier flaps is shown.

Figure 2:
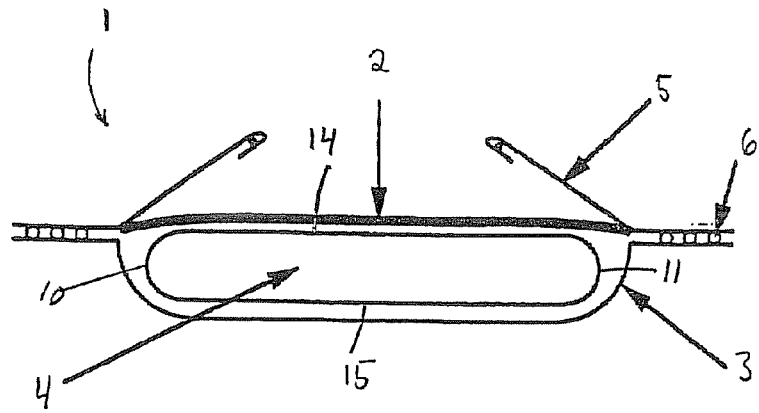
Figure 3:
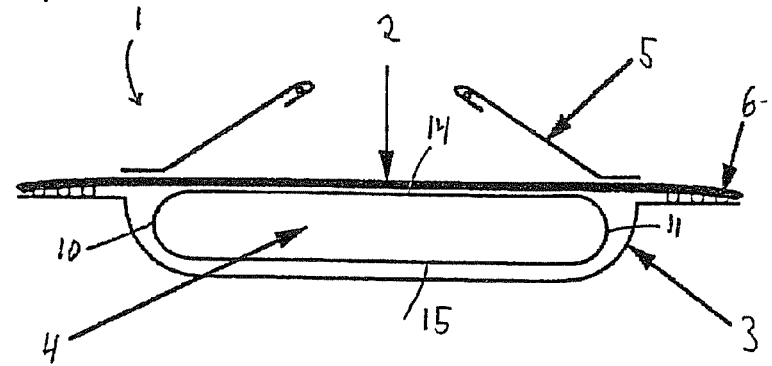

In FIGS. 2 and 3 two conventional diapers with barrier flaps are shown in cross-section.

Figure 4:
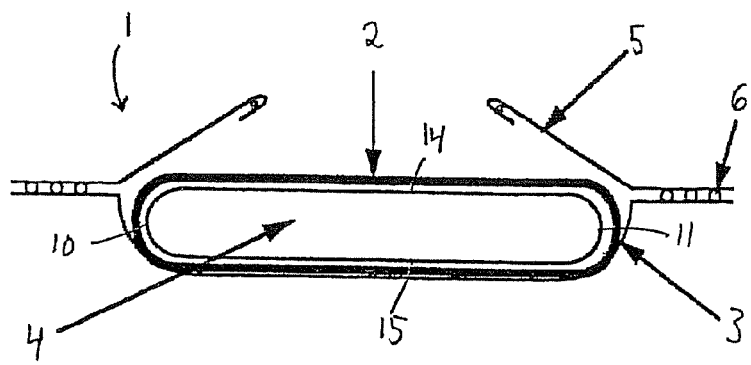

In FIG. 4 a diaper according to an embodiment of the invention is shown in cross section.

Figure 5:
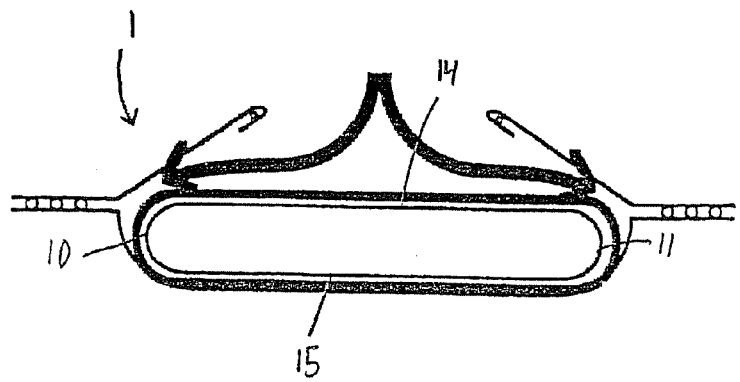

In FIG. 5 it is shown how given-off urine from a wearer is distributed around the absorbent core in the diaper of the invention.

Figure 6:
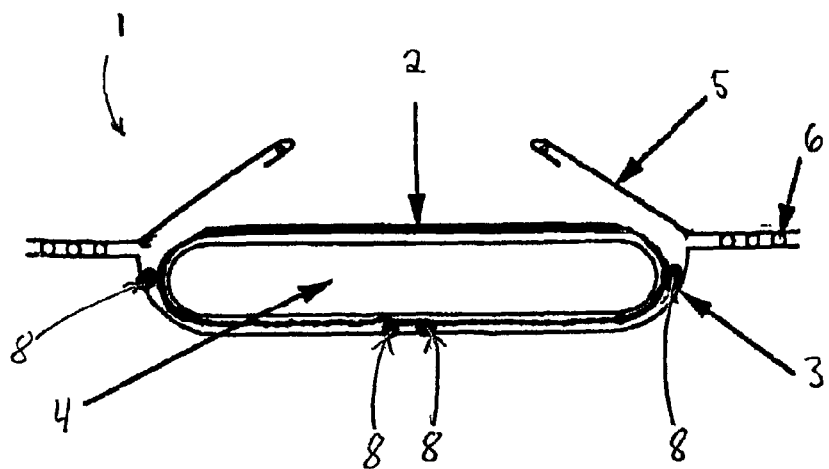

In FIG. 6 an embodiment of the diaper according the invention having point connections is shown.

DETAILED DESCRIPTION OF THE PREFERRED EMBODIMENTS

In FIG. 1 a conventional diaper (1) is shown, and in FIGS. 2 and 3 a cross section of two conventional diapers are shown (1). They are equipped with a fluid permeable top sheet (2) facing the wearer, and a fluid impermeable backing sheet (3) facing away from the wearer. Between these sheets an absorbent core (4) is placed. The absorbent core has an upper side (14), a bottom side (15), two longitudinally running sides (10, 11) and two laterally running sides (12, 13). Further, the diapers are equipped with barrier flaps (5) running longitudinally along the side edges of the absorbent core, which flaps face the wearer, in order to prevent fluid leakage. Moreover, the diapers are equipped with leg elastics (6) running longitudinally along the outside of the diaper. The barrier flaps may for example, as in FIG. 2, extend out to the leg elastics, or, as in FIG. 3, be welded or glued onto the top sheet. In this case the top sheet extends out to the leg elastics. The top sheet and the backing sheet are attached to each other along the side of the absorbent core, in order to prevent leakage in that direction, and for the absorbent core to stay in its position.

In FIG. 4 a diaper according to an embodiment of the invention is shown. It differs from the diapers described in FIG. 1, 2 and 3 in that the top sheet (2) also extends down along the sides of the absorbent core (4), and, as in this embodiment, also covers the bottom side of the absorbent core. The barrier flap (5) extends to the leg elastics. The top sheet and the backing sheet are attached to each other on the bottom side of the absorbent core. Hereby, given-off urine (FIG. 5) may distribute around almost the entire absorbent core, which increases the fluid gathering volume and increases the area through which the fluid may be let in to the absorbent core.

The fluid permeable top sheet (2) is manufactured from a soft skin-friendly material. For example it can be manufactured from a non-woven material, having a soft and smooth surface, such as for example a spun-bond of polypropylene fibres. In order to keep the surface closest to the wearer dry, a hydrophobic non-woven material may be used, which is equipped with holes in such a way that openings are created in the material, whereby the openings are greater than the cavities between the fibres in the material. Hereby, fluid may get through the openings of the top sheet to the underlying absorbent core. Other examples of material in the top sheet may for example be plastic films equipped with holes, such as a polyethylene film equipped with holes. All materials that are used for top sheets in absorbent products may be used for the top sheet in the present invention, and the above mentioned materials are only given as examples.

The backing sheet (3) may consist of a fluid impermeable and elastic material, preferably a thin plastic film of PE, PP or a polyester, but it may also consist of a laminate of a fluid permeable material, such as a non-woven, and a fluid impermeable material. All materials that are used as backing sheet materials are possible. The backing sheet may preferably be air permeable.

The top sheet may be connected to the backing sheet and to the absorbent core by, for example, glue, or some other kind of thermal connection, one or more weld joints, one or more hook-and-loop connections, or in some other way that in a good way connects the top sheet to the backing sheet. This connection may be performed so that the top sheet is bound to the entire backing sheet, or so that only the front and the rear side or the front and the rear edge, for example in line with the laterally running sides (12, 13) of the absorbent core, or so that the top sheet is bound by point connections to the backing sheet, or so that the top sheet is bound to the backing sheet by a longitudinally running connection in the middle of the backing sheet, or in any other way which provides a sufficiently good connection for fulfilling the purposes of the invention.

Further, as described in FIG. 6, the top sheet may be attached to the backing sheet by point connections (8). The number of point connections (8) may be from only one point connection to a large number of point connections. For example, one point connection at the front and one at the rear part of the top sheet may be used, or one point connection at each side of the absorbent core, or a combination of these variants. Moreover, large number of point connections may be used simultaneously, for example in some kind of pattern. Many other variants are fully possible as long as they provide a sufficiently good connection between the top sheet and the backing sheet.

In yet another embodiment a so-called multiple-use chassis may be used. In this embodiment the chassis serves the function of the backing sheet, and is also equipped in such a way that it may be re-used. The barrier flaps may optionally be attached to the top sheet in this embodiment. The absorbent core with the surrounding top sheet is attached to the chassis at use and may then be changed for a new absorbent core/top sheet after use. The attachment of the top sheet to the backing sheet is suitably designed in such a way that the top sheet and the absorbent core easily are unfastened from the backing sheet, and easily are put there, whereby the top sheet with the absorbent core still is sufficiently stably attached to the chassis. In a variant of this embodiment, the attachment of the top sheet to the backing sheet is made up of a hook-loop-connection, but also other connections may be used.

The absorbent core or body (4) is preferably composed of one or more layers of cellulose fibres, such as cellulose fluff pulp. Other materials that may be used are for example absorbing non-woven material, foam material, synthetic fibre material or peat. In addition to cellulose fibres or other absorbing materials, the absorbent core may also comprise superabsorbent material, so called SAP (superabsorbent polymers), i.e. material in the form of fibres, particles, granules, films or the like, which have the capacity to absorb fluid in an amount of several times their own weight. The superabsorbent material binds the fluid and forms a fluid containing gel. Moreover, the absorbent core may comprise binders, form stabilising components, and the like. Additional absorbing layers, which thereby improve the absorbing properties, may also be used, such as various fluid spreading material layers and insets, so called wads. The absorbent core may be treated chemically or physically in order to change the absorbent properties. For example, it is possible to provide an absorbent layer having compressions, in order to control the liquid flow in the absorbent core. It is also possible to enclose the absorbent layer(s) in a casing of, for example, tissue material. Furthermore, the absorbent core may be hour-glass shaped, or it may also have straight side edges so that the core is essentially rectangular.

Moreover, the absorbent core according to the present invention may be designed in such a way that it has an improved fluid-inlet in those parts of the body that faces the side and the bottom part of the absorbent core. The fluid inlet may for example be improved by using various types of wetting agents or treatments, either involving the core or the surface material. For example, a hydrophobic top material such as polypropylene may be treated with a wetting agent so that it acquires a hydrophilic surface. It is also possible to use hydrophilic materials such as viscose-rayon or tissue in parts of the core or for the top material. In this way, the absorption capacity of the core is adapted to the design of the top sheet.

The main purpose of the barrier flaps (5) is to prevent fluid leakage from the absorbent product. Therefore, it is important that they have a good fit to the wearer of the diaper. The barrier flaps have a proximal edge, which is close to the absorbent core, and a free distal edge, which lies against the body of the wearer, and which includes the elastic means. Preferably, the barrier flaps extend along the entire length of the absorbent core, but in some cases that may be unnecessary, as long as they provide a secure leakage protection. The height of the barrier flaps is preferably 10-50 mm, and the proximal edge as well as the distal edge may be connected to the top sheet in the front and rear ends of the product.

The barrier flaps are kept standing with the elastic means, which preferably runs along the distal edge inside the flap. This elastic means may be of any kind that is conventional in the art, which fits in the flap, and which rises the barrier flap over the surface of the absorbent core and also makes the absorbent product suit the wearer. The elastic means may for example comprise elastic rubber bands.

The leg elastics (6) may for example be composed of one or more elastic threads or bands, which preferably lie between the backing sheet and the material of the barrier flap along the sides of the diaper, at least in the middle part of the diaper, longitudinally seen, and be attached to the backing layer and/or the barrier flap in a stretched state.

Moreover, the absorbent product is equipped with a fastening system, which is meant to connect the front and rear parts to each other at use, in order to keep the product in position in a reliable and comfortable way. For example, the fastening system may be of hook-loop type. The product may also be of a pants diaper type, in which case it is not equipped with a conventional fastening system.

Further modifications of the embodiments above are of course possible, which modifications also are encompassed by the scope of the invention.

Although only preferred embodiments are specifically illustrated and described herein, it will be appreciated that many modifications and variations of the present invention are possible in light of the above teachings and within the purview of the appended claims without departing from the spirit and intended scope of the invention.

The invention claimed is:

1. An absorbent product having a longitudinal direction extending from a front portion to a rear portion, and a lateral direction that is substantially perpendicular to the longitudinal direction, the absorbent product comprising:
    a fluid impermeable backing sheet facing away from a wearer at use, an absorbent core positioned between the wearer and the backing sheet, which absorbent core has an upper side, facing the wearer at use, a bottom side, facing away from the wearer at use, two longitudinally running sides extending along longitudinal edges of the absorbent core, and two laterally running sides extending along lateral edges of the absorbent core,
    two longitudinally running barrier flaps at the longitudinally running sides of the absorbent core, the longitudinally running barrier flaps are directly connected to the backing sheet at the longitudinally running sides of the absorbent core, and
    a fluid permeable top sheet, wherein:
        the top sheet covers the upper side of the absorbent core,
        the top sheet, in addition to the upper side of the absorbent core, also covers at least the longitudinally running sides of the absorbent core and a part of the bottom side of the absorbent core,
        the top sheet extending between the part of the bottom side of the absorbent core and the backing sheet,
        the top sheet has at least one connection to the backing sheet at the part of the bottom side of the absorbent core,
        the top sheet is attached to the backing sheet only at the lateral running sides of the absorbent core, the top sheet adapted to contact the wearer during use of the absorbent product, and
        the connection between the top sheet and the backing sheet is made up of at least one glued joint, at least one weld joint or at least one hook-and-loop connection.

2. The absorbent product according to claim 1, whereby the top sheet covers the entire bottom side of the absorbent core.

3. The absorbent product according to claim 1, whereby the connection between the top sheet and the backing sheet is made up of at least one point connection.

4. The absorbent product according to claim 1, wherein the absorbent product is a diaper or an incontinence device.

5. The absorbent product according to claim 1, wherein the connection between the top sheet and the backing sheet is made up of at least one glued joint.

6. The absorbent product according to claim 1, wherein the connection between the top sheet and the backing sheet is made up of at least one weld joint.

7. The absorbent product according to claim 1, wherein the connection between the top sheet and the backing sheet is made up of at least one hook-and-loop connection.

8. The absorbent product according to claim 1, wherein the absorbent core is at least partially enclosed by the top sheet, and the absorbent core is further enclosed by a casing.

9. An absorbent product comprising a fluid permeable top sheet, a fluid impermeable backing sheet facing away from a wearer at use, an absorbent core positioned between the wearer and the backing sheet, which absorbent core has an upper side facing the wearer at use, a bottom side facing away from the wearer at use, two longitudinally running sides and two laterally running sides, the product further comprises two longitudinally running barrier flaps at the longitudinally running sides of the absorbent core, and the top sheet covers the upper side of the absorbent core, and the top sheet, in addition to the upper side of the absorbent core, also covers at least the longitudinally running sides of the absorbent core and a part of the bottom side of the absorbent core, the top sheet extending between at least a portion of the bottom side of the absorbent core and the backing sheet and the top sheet has at least one connection to the backing sheet at the bottom side of the absorbent core, and the barrier flaps are directly connected to the backing sheet at the longitudinally running sides of the absorbent core,
    whereby the top sheet is attached to the backing sheet only at the lateral running sides of the absorbent core, and
    whereby the connection between the top sheet and the backing sheet is designed in such a way that essentially the whole part of the top sheet, that covers the bottom side of the absorbent core, is attached to the backing sheet.

10. The absorbent product according to claim 9, whereby the top sheet covers the entire bottom side of the absorbent core.

11. The absorbent product according to claim 9, whereby the connection between the top sheet and the backing sheet is made up of at least one point connection.

12. The absorbent product according to claim 9, whereby the connection between the top sheet and the backing sheet is made up of at least one glued joint, at least one weld joint or at least one hook-and-loop connection.

13. The absorbent product according to claim 9, wherein the absorbent product is a diaper or an incontinence device.

14. The absorbent product according to claim 9, wherein the absorbent core is at least partially enclosed by the top sheet, and the absorbent core is further enclosed by a casing.

* * * * *